United States Patent
Tiwari et al.

(10) Patent No.: US 12,391,966 B2
(45) Date of Patent: Aug. 19, 2025

(54) BIOPOLYMER FILM AND METHOD OF PREPARING THE SAME

(71) Applicant: School of Biotechnology, Rajiv Gandhi Proudyogiki Vishwavidyalay, Bhopal (IN)

(72) Inventors: Archana Tiwari, Bhopal (IN); Riddhi Tiwari, Bhopal (IN); Roopesh Jain, Hyderabad (IN); Amandeep Girdhar, Philadelphia, PA (US)

(73) Assignee: SCHOOL OF BIOTECHNOLOGY, RAJIV GANDHI PROUDYOGIKI VISHWAVIDYALAY, Bhopal (IN)

( * ) Notice: Subject to any disclaimer, the term of this patent is extended or adjusted under 35 U.S.C. 154(b) by 389 days.

(21) Appl. No.: 17/338,596

(22) Filed: Jun. 3, 2021

(65) Prior Publication Data
US 2021/0381012 A1    Dec. 9, 2021

(30) Foreign Application Priority Data
Jun. 3, 2020   (IN) ............................. 202021023221

(51) Int. Cl.
| | | |
|---|---|---|
| C12P 7/625 | (2022.01) | |
| C08J 5/18 | (2006.01) | |
| C08L 1/14 | (2006.01) | |
| C08L 67/04 | (2006.01) | |

(52) U.S. Cl.
CPC ............... *C12P 7/625* (2013.01); *C08J 5/18* (2013.01); *C08L 1/14* (2013.01); *C08L 67/04* (2013.01); *C08J 2301/14* (2013.01); *C08J 2401/02* (2013.01); *C08J 2467/04* (2013.01)

(58) Field of Classification Search
CPC .......... C12P 7/625; C08J 5/18; C08J 2301/14; C08J 2401/02; C08J 2467/04; C08J 2367/04; C08L 1/14; C08L 67/04; C12R 2001/01
See application file for complete search history.

(56) References Cited

U.S. PATENT DOCUMENTS

| | | | | |
|---|---|---|---|---|
| 9,040,267 B2* | 5/2015 | Herrema | .................. | C12P 7/625 |
| | | | | 435/135 |
| 10,378,030 B2* | 8/2019 | Herrema | .................. | C12P 7/625 |
| 2014/0330032 A1* | 11/2014 | Lynch | .................... | C12P 7/6409 |
| | | | | 435/252.33 |

FOREIGN PATENT DOCUMENTS

WO    WO-2020037394 A1 *  2/2020  ............. C08J 11/00

OTHER PUBLICATIONS

Sobek, J. et al., Endogenous metabolism of Azotobacter agilis. J. Bacteriol. 92, pp. 687-695, 1966 (esp. Methods—p. 688) (Year: 1966).*
Ceccorulli et al., "Effect of a Low Molecular Weight Plasticizer on the Thermal and Viscoelastic Properties of Miscible Blends of Bacterial Poly(3-hydroxybutyrate) with Cellulose Acetate Butyrate", Macromolecules, 26: 6722-26, 1993 (pp. 6722-6723 and Figure 2) (Year: 1993).*
Verlinden, et al., "Production of polyhydroxyalkanoates from waste frying oil by Cupriavidus necator". AMB Expr. 1, 11, 2011 (Entire Document) (Year: 2011).*
Rana et al., "Functional properties, phenolic constituents and anti-oxidant potential of industrial apple pomace for utilization as active food ingredient." Food Science and Human Wellness 4.4 (2015): 180-187, 2015, (esp. p. 181, Methods—2.3.) (Year: 2015).*
Chen et al., "Effects of ethyl cellulose on the crystallization and mechanical properties of poly(3-hydroxybutyrate)", Int. J. Biol. Macromol. 88, 2016 (esp. Abstract, Figure 10, and Conclusions—p. 128) (Year: 2016).*
Md Badrul Hisham et al. "Production of Biosurfactant Produced from Used Cooking Oil by Bacillus sp. HIP3 for Heavy Metals Removal",. Molecules.; 24(14):2617, 2019, (esp. Methods section, p. 10) (Year: 2019).*
Rebocho, et al., Preparation and Characterization of Films Based on a Natural P(3HB)/mcl-PHA Blend Obtained through the Co-culture of Cupriavidus Necator and Pseudomonas Citronellolis in Apple Pulp Waste. Bioengineering (Basel), 5;7(2):34, Apr. 2020 (Entire Document) (Year: 2020).*
Zhang et al. "Miscibility, thermal behaviour and morphological structure of poly (3-hydroxybutyrate) and ethyl cellulose binary blends". Polymer. Oct. 1, 1997;38(21):5379-87 (Year: 1997).*
El-Shafee et al. "Miscibility, crystallization and phase structure of poly (3-hydroxybutyrate)/cellulose acetate butyrate blends". European Polymer Journal. Oct. 1, 2001;37(10):2091-104 (Year: 2001).*
McGuinness-Hickey, M. "Elongation at Break—Definition, Testing, Material Selection", hzo.com, Published Sep. 19, 2023. <URL:https://hzo.com/blog/elongation-at-break-definition-testing-material-selection> Accessed on Nov. 12, 2024, 5 pages. (Year: 2023).*
Parmar and Rupasinghe, "Optimization of dilute acid-based pre-treatment and application of laccase on apple pomace", Bioresource Technology 124,433-39, 2012 (esp. pp. 434-435) (Year: 2012).*
Rana et al., "Fuctional Properties, phenolic constituents and anti-oxidant potential of industrial apple pomace for utilization as active food ingredient." Food Science and Human Wellness 4.4 (2015): 180-187, 2015, (esp. p. 181, Methods—2.3.) (Year: 2015.*
Rebocha et al., Preparation and Characterization of Films Based on a Natural P(3HB)/mcl-PHA Blend Obtained through the Co-culture of Cupriavidus Necator and Pseudomonas Citronellolis in Apple Pulp Waste. Bioengineering (Basel), 5;7(2):34, Apr. 2020 (Entire Document) (Year: 2020).*

(Continued)

*Primary Examiner* — Aaron J Kosar
*Assistant Examiner* — Andrew T Moehlman
(74) *Attorney, Agent, or Firm* — Kunzler Bean & Adamson

(57) ABSTRACT

A method of producing biopolymer films is disclosed. The method includes pre-treating a carbon source, preparing a basal media, preparing an inoculum and fermenting the carbon source using the inoculum in the basal media so as to selectively modify the metabolic pathway of the microorganism to produce a biopolymer. Further, the method includes recovering the biopolymer resulting from the step of fermentation and blending the biopolymer with at least one blending agent to produce one or more biopolymer films.

9 Claims, 1 Drawing Sheet

(56) References Cited

OTHER PUBLICATIONS

McGuiness-Hickey, M. "Elongation at Break—Definition, Testing, Material Selection", hzo.com, Published Sep. 19, 2023.<URL:https://hzo.com/blog/elongation-at-break-definition-testing-material-selection> Accessed on Nov. 12, 2024, 5 pages. (Year: 2023).*

* cited by examiner

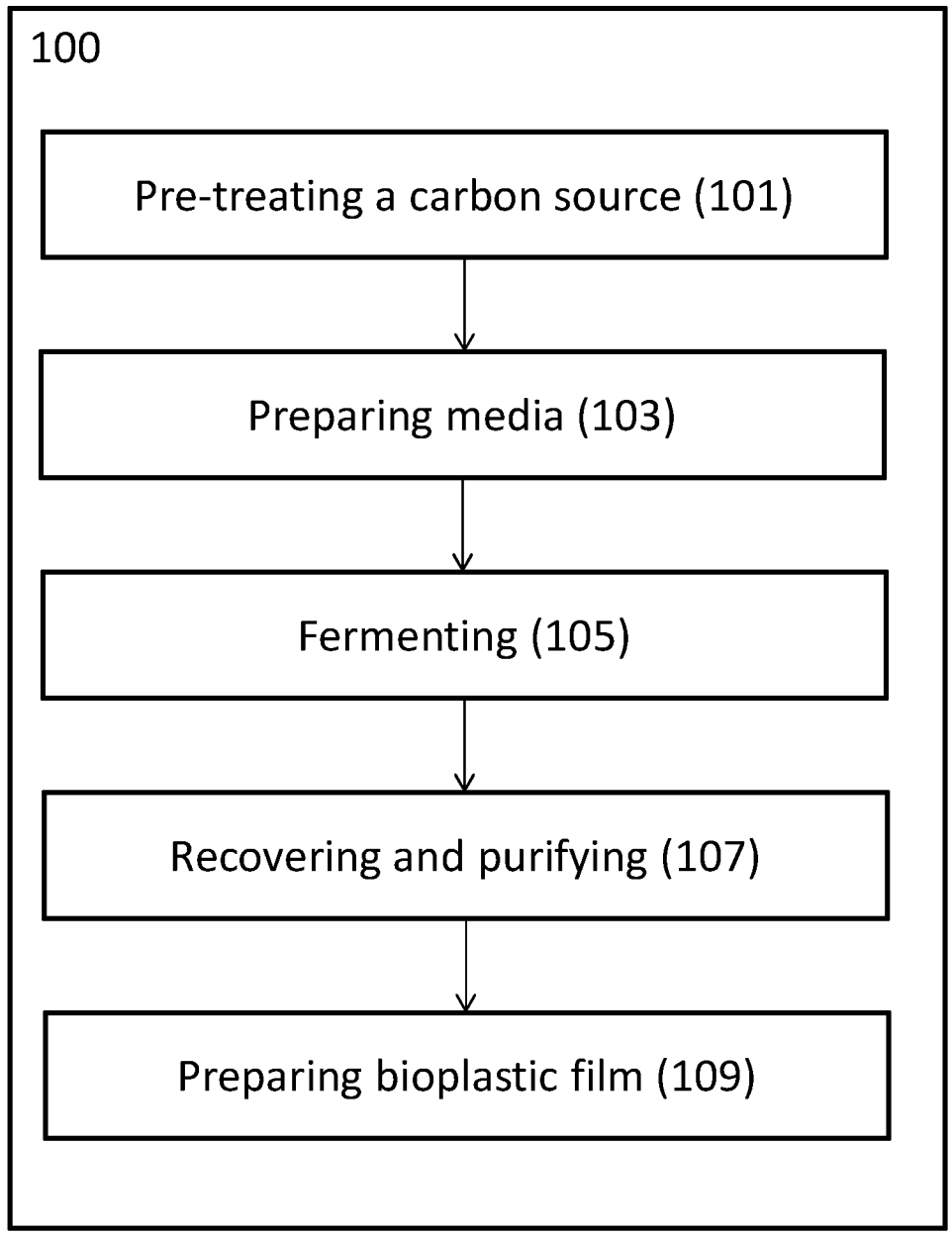

BIOPOLYMER FILM AND METHOD OF PREPARING THE SAME

CROSS REFERENCES TO RELATED APPLICATIONS

This application claims priority to Indian Patent Application Number 202021023221 entitled "BIOPOLYMER FILM AND METHOD OF PREPARING THE SAME" and filed on Jun. 3, 2020, for Archana Tiwari, et al., which is incorporated herein by reference in its entirety for all purposes.

FIELD OF INVENTION

The present invention relates to a biopolymer. More specifically, the present invention relates to a biopolymer film prepared from a waste carbon source.

BACKGROUND

Biopolymer is an eco-friendly alternative to synthetic plastic. Biopolymer is made of bio-degradable components. Such biopolymers produced in nature are called Polyhydroxyalkanoates (PHAs).

Biopolymers are mostly produced either by microbes or plants. However, the efforts to produce biopolymers from plant cells has not achieved much success as high yield of polymers is limited by slow growth and development of plants thereby resulting in low yields (<10% (w/w) of dry cell weight) of polymers. On the other hand, PHAs can be accumulated up to 90% (w/w) in bacterial cells and are thus a priority because of the ease in culturing and being economical, in contrast to the complex plant system. PHAs accumulation is an inherent response to the stress conditions faced by bacterial cells. The same are generated in vitro by exposing bacteria to nutrient limitations, due to which they switch their metabolic pathways and cause PHA production as their carbon and energy reserves.

Conventionally, PHAs are produced from noble carbon sources. However, the use of such raw materials increases the cost of production. Raw material accounts for 40-48% of total production cost, of which 70-80% cost is due to carbon sources, which is a major cause of cost hike and thereby limits its commercial use. Moreover, use of inferior carbon source has resulted in poor yield because of poor optimization of fermentation condition.

Natural PHAs have undesirable qualities like they are compostable only under specific conditions, its brittleness, dominant hydrophilic character and unsatisfactory mechanical properties particularly, under wet environments. Further, the biopolymer available does not meet the standards for biopolymers set by International Organization for Standardization (ISO) and American Standard for Testing of Materials (ASTM).

Therefore, there arises a requirement of a method to produce biopolymer which overcomes the aforementioned challenges associated with the conventional methods.

SUMMARY

The present invention discloses a method of producing biopolymer films. The method in turn includes pre-treating a carbon source, preparing a basal media, preparing an inoculum and fermenting the carbon source using the inoculum in the basal media so as to selectively modify the metabolic pathway of the microorganism to produce a biopolymer, recovering the biopolymer resulting from the step of fermentation and blending the biopolymer with at least one blending agent to produce one or more biopolymer films.

More specifically, the present invention relates to a biopolymer film prepared from a waste carbon source. The foregoing features and other features as well as the advantages of the invention will become more apparent from the following detailed description, which proceeds with reference to the accompanying FIGURES.

BRIEF DESCRIPTION OF DRAWINGS

The summary above, as well as the following detailed description of illustrative embodiments, is better understood when read in conjunction with the apportioned drawings. For the purpose of illustrating the present disclosure, exemplary constructions of the disclosure are shown in the drawings. However, the disclosure is not limited to specific methods and instrumentalities disclosed herein. Moreover, those in the art will understand that the drawings are not to scale.

FIG. 1 depicts a method 100 to prepare a biopolymer film in accordance with an embodiment of the present invention.

DETAILED DESCRIPTION OF THE DRAWINGS

Prior to describing the invention in detail, definitions of certain words or phrases used throughout this patent document will be defined: the terms "include" and "comprise", as well as derivatives thereof, mean inclusion without limitation; the term "or" is inclusive, meaning and/or; the phrases "coupled with" and "associated therewith", as well as derivatives thereof, may mean to include, be included within, interconnect with, contain, be contained within, connect to or with, couple to or with, be communicable with, cooperate with, interleave, juxtapose, be proximate to, be bound to or with, have a property of, or the like; Definitions of certain words and phrases are provided throughout this patent document, and those of ordinary skill in the art will understand that such definitions apply in many, if not most, instances to prior as well as future uses of such defined words and phrases.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Although the operations of exemplary embodiments of the disclosed method may be described in a particular, sequential order for convenient presentation, it should be understood that the disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed herein. Moreover, for the sake of simplicity, the attached FIGURES may not show the various ways in which the disclosed system, method, and apparatus can be used in combination with other systems, methods, and apparatuses.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments. These features and advantages of the embodiments will become more fully apparent from the following description and apportioned claims, or may be learned by the practice of embodiments as set forth hereinafter.

In accordance with the present disclosure, a biopolymer film and a method for preparing thereof is disclosed. In an embodiment, the biopolymer film includes polyhydroxybutyrate (PHB) and a blending agent. The biopolymer film of the present invention may be used as an alternative to synthetic plastic. The biopolymer films of the present invention are derived by following a pre-defined method which includes various steps such as pre-treatment of carbon source, media preparation, fermentation, recovery and purification and blending. The carbon sources used in the present invention include waste carbon sources such as waste frying oil or apple pomace hydrolysate. The use of waste carbon sources for production of biopolymer films reduces the cost of production thereby making the method cost-effective.

The fermentation of waste carbon sources is performed using a pre-defined microorganism cultivated in a basal media so as to selectively modify the metabolic pathway of the microorganism to yield a biopolymer. In an embodiment, the microorganism used in the present invention is *Cupriavidus necator*.

Further, the method of producing the biopolymer film includes blending the biopolymer with a least one blending agent. In an embodiment, the biopolymer is blended with ethyl cellulose in the ratio of 90:10. Such blending resulted in increase in the tensile strength by 36.5% than pure PHB.

FIG. 1 outlines the method 100 to prepare a biopolymer film (not shown). The first step 101 of the said method includes pre-treatment of a raw material. The raw material in the present invention may be a waste carbon source including without limitation waste frying oil or apple pomace hydrolysate. The waste frying oil corresponds to residual oil after cooking. The pre-treatment of waste frying oil may include sterilization of the waste frying oil. The process of sterilization may be performed by any means known in the art. In an embodiment, the waste frying oil is filter sterilized by passing the waste frying oil through a 0.22 micron filter.

Apple pomace hydrolysate may be prepared from waste apple pomace discarded by juice industries. For pre-treatment, the pomace may be reconstituted in water and filtered to separate any residual pulp. The reconstituted pomace pulp may be filtered using a stainless steel sieve of 20 mesh. Other filtration technique known in the art may also be used instead. In an embodiment, the filtrate is thereafter spread on a tray and dried for about a day at 55-60° C. The dried filtrate is then grinded to powder form. The powder as obtained is hydrolyzed by treating the powder with an acid at 100° C. for 15 min. The lysate as obtained is neutralized and sterilized. The acid may include any common acid having a pH ranging from 1.0 to 2.0. The lysate may be neutralized using any known alkali. The neutralized lysate may be sterilized by any known method in the art. In an embodiment, the powder is hydrolyzed using 0.75 wt % Sulfuric acid solution having a pH of 1.1 and thereafter neutralized with 0.5N Sodium hydroxide solution. In a preferred embodiment, the neutralized lysate is sterilized by autoclaving at 121° C., 15 psi.

At step 103, a basal media is prepared. The basal media may be prepared by dissolving a plurality of salts known in the art in distilled water. The plurality of salts used in the basal media and associated concentration may be dependent upon optimum biomass and/or biopolymer production. In an embodiment, the plurality of salts may include without limitation, $K_2HPO_4$, $KH_2PO_4$, $KNO_3$, $(NH_4)_2SO_4$, $MgSO_4 \cdot 7H_2O$ and NaCl. As an example, salts and distilled water can be dissolved in a ratio of 1:1000. The basal media may have a pre-defined pH say, a neutral pH. The basal media may be sterilized by methods known in the art. In an embodiment, the basal media is sterilized by autoclaving at 121° C., 15 psi.

At step 105, the process of fermentation takes place to produce biopolymer. The materials required for fermentation include a microbial inoculum, a basal media and a carbon source. Prior to the fermentation, a microbial inoculum may be prepared to facilitate the production of the biopolymer. A pure culture or a consortium culture of a pre-defined microorganism may be used to ferment the raw material. In an embodiment, a pure culture of *Cupriavidus necator* (MTCC 1285) is used in the present invention. The said culture was obtained from Microbial Type Culture Collection and Gene Bank, Institute of Microbial Technology, Chandigarh, India. The pure culture may utilize the raw material as a carbon source to finally yield the biopolymer.

As an exemplary process, a lyophilized pure culture is revived on a solid nutrient media at pre-defined physiological conditions for the microorganism. Thereafter, a microbial inoculum is prepared by adding a loop of cells to nutrient broth and cultured for a day or two on a rotatory shaker. In an embodiment, the microbial inoculum is prepared in a 250 mL conical flask by incubating a loop of *Cupriavidus necator* cells in 100 mL sterilized tryptone soy broth (pH 7.0) at 30° C. for 36 hours on a rotary shaker (150 rpm).

The prepared microbial inoculum and the pre-treated waste carbon source may be added to the basal media as prepared at step 103 prior to fermentation. The microbial inoculum may be added in the range of 5% to 15%. The amount of waste carbon source may be added such that the biopolymer obtained post fermentation is maximum. The waste carbon source may be added in the range of 1% to 3%. In an embodiment, 10% microbial inoculum and 2% waste carbon source is added to the basal media.

The fermentation may occur at a pre-defined initial culture pH, culture temperature and agitation speed inside a bioreactor known in the art. The initial culture pH may range from 6 to 7.5. The culture temperature may range from 28° C. to 37° C. The agitation speed may range from 150 rpm to 250 rpm. The fermentation may proceed for 48-72 hr. In a preferred embodiment, the fermentation is done inside a batch bioreactor at 7.0 initial culture pH, 30° C. culture temperature and 200 rpm agitation speed for 72 hr.

At step 107, recovery and purification of the biopolymer takes place. Post fermentation, the fermented broth may be centrifuged to harvest and wash the cells. In an embodiment, the centrifuge is operated at 10,000 rpm for 15 min. The cells may be washed using without limitation distill water.

The cells harvested may be lysed with methods known in the art. In a preferred embodiment, the cells are lysed using a 5% sodium hypochlorite solution at 37° C. for 90 min in a shaker. Other lysing methods may be implemented for complete digestion of a cell and cell components except the biopolymer present inside the cells stays intact.

The cell lysate so obtained may be centrifuged to separate the biopolymer. In an embodiment, the centrifuge is operated at 8000 rpm, 4° C. for 20 min. The supernatant may be discarded. The pellet may be washed and centrifuged multiple times to remove any impurities. In an embodiment, the pellet is first washed with distill water followed by a 1:1 mixture of acetone and methanol followed by distil water again.

The washed biopolymer may be dissolved in an organic solvent and spread on a surface. In an embodiment, the organic solvent is chloroform heated at 60° C. Further, the powdered biopolymer may be obtained by evaporating the organic solvent. In one embodiment, the organic solvent is evaporated by air drying the biopolymer at room temperature for 24 hr. In another embodiment, the organic solvent is evaporated inside an oven for 24 hr. The oven may be operated in a temperature ranging from 35° C. to 40° C.

At step 109, one or more biopolymer films are prepared using the biopolymer. The biopolymer as obtained may be blended with at least one blending agent in various ratios to induce a range of physical properties to the biopolymer. The blending agent may include without limitation ethyl cellulose (EtC) or cellulose acetate butyrate (CAB). However, other blending agents also lie within the scope of the present invention.

The ratio between the biopolymer and the blending agent may include 50:50, 60:40, 70:30, 80:20 and 90:10. The blended biopolymer may be prepared by dissolving the biopolymer and the blending agent in respective ratios in an organic solvent. The organic solvents may include without limitation, toluene, acetone, chloroform, ethylene carbonate, or a combination thereof. The solution may then be spread on an even surface to slowly evaporate the organic solvent, preferably chloroform. In an embodiment, the even surface includes a glass plate. After evaporation of the organic solvent, a biopolymer film may be obtained in the form of dull white precipitate. In an embodiment, the biopolymer is made of PHB and EtC in the ratio of 90:10. In another embodiment, the biopolymer is made of PHB and CAB in the ratio of 50:50. The 90:10 blend of PHB and EtC along with 50:50 blend of PHB with CAB may have superior properties compared to other blending ratios.

The biopolymer film obtained from the above process possesses biodegradability along with mechanical properties as defined by International Organization for Standardization (ISO) and American Standard for Testing of Materials (ASTM) standards as well. With respect to the standards outlined above, 90:10 blend of biopolymer with ethyl cellulose manifests increase in modulus of elasticity. Similarly, the 50:50 blend of the biopolymer with Cellulose acetate butyrate manifests increase in modulus of elasticity, with an increment of 1.6 times for elongation at break.

The above described invention may be further supported by the following example:

Example 1: The biopolymer PHB was prepared by fermenting 2% apple pomace hydrolysate in a basal media. Pure culture of Cupriavidus necator was used as an inoculum for the fermentation. The fermentation process was carried out inside a batch bioreactor at 7.0 initial culture pH, 30° C. culture temperature and 200 rpm agitation speed for 72 hr. Post fermentation, the cells were harvested by centrifugation at 10,000 rpm for 15 min. The cells were further washed with distil water. The washed cells were lysed by incubating the cells with 5% solution of sodium hypochlorite at 37° C. for 90 min. The lysate was then centrifuged at 8000 rpm, 4° C. for 20 min to separate the PHB granules. The PHB granules were washed multiple times to remove any impurities. The first wash was done with distil water followed by a 1:1 mixture of acetone and methanol and then distil water again. The PHB was then dissolved in chloroform at 60° C. and spread over a glass plate. The glass plate was then left at room temperature for 24 hr to evaporate all the chloroform and obtain PHB. The yield of PHB obtained is 58%. Thereafter, films of the PHB were prepared. The characterization of different PHB biopolymer films is provided in the below table:

| Property | Pure PHB | PHB + EtC (90:10) | PHB + CAB (50:50) |
| --- | --- | --- | --- |
| Tensile strength | 4.362 ± 0.543 | 6.864 ± 1.041 | 20.351 ± 5.019 |
| Elongation at break | 3.299 ± 0.677 | 2.242 ± 0.723 | 5.214 ± 1.338 |
| Modulus | 298.559 ± 33.549 | 570.082 ± 43.552 | 719.474 ± 84.788 |
| Percentage weight loss at about 172° C. | 95.4% | 96.64% | 96.94% |
| Bio-degradation after 6 months | 63% | 71% | 31.74% |

The blending induced ductility to PHB by reducing stiffness and fragility of the film.

The scope of the invention is only limited by the appended patent claims. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

We claim:

1. A method of producing biopolymer films comprising:
   pre-treating a carbon source to obtain an apple pomace lysate by:
      reconstituting and filtering a waste apple pomace to form a filtrate;
      drying the filtrate for a day at 55-60° C.;
      grinding the dried filtrate to form a powder; and
      hydrolyzing the powder with an acid at 100° C. for 15 min to form lysate; and
   sterilizing the lysate to form the apple pomace lysate;
   preparing a basal media;
   preparing an inoculum, wherein the inoculum includes a pure culture of *Cupriavidus necator*, adding the apple pomace lysate and the inoculum in the basal media so as to selectively modify the metabolic pathway of the *Cupriavidus necator* therein;
   fermenting the apple pomace lysate with the inoculum in the basal media to produce a biopolymer;
   recovering the biopolymer resulting from the step of fermentation; and
   blending the recovered biopolymer with at least one blending agent by:
      dissolving the biopolymer and at least one of ethyl cellulose (EtC) or cellulose acetate butyrate (CAB) in a ratio of 50 parts of the biopolymer with 50 parts of cellulose acetate butyrate (CAB), or 90 parts of the biopolymer with 10 parts of ethyl cellulose (EtC) in an organic solvent; and evaporating the organic solvent to produce one or more biopolymer films, wherein the biopolymer film is a mixture of polyhydroxybutyrate (PHB) and a blending agent;

wherein, the biopolymer film having 90 parts of polyhydroxybutyrate (PHB) with 10 parts ethyl cellulose (EtC), the biopolymer film, by percent thereof, biodegrades at least 71% within 6 months; and wherein the biopolymer film having 50 parts of polyhydroxybutyrate (PHB) with 50 parts cellulose acetate butyrate (CAB), the biopolymer film provides elongation at break ranging from 3.876% to 6.552%.

2. The method as claimed in claim 1 wherein the hydrolyzing includes hydrolyzing the powder using 0.75 wt % sulfuric acid solution having a pH of 1.1 and thereafter neutralizing the powder with 0.5N sodium hydroxide solution.

3. The method as claimed in claim 1 wherein the sterilizing the lysate includes sterilizing the neutralized lysate by autoclaving at 121° C. and 15 psi.

4. The method as claimed in claim 1 wherein the preparing the basal media includes dissolving a plurality of salts in distilled water.

5. The method as claimed in claim 4 wherein the plurality of salts include $K_2HPO_4$, $KH_2PO_4$, $KNO_3$, $(NH_4)_2SO_4$, $MgSO_4 \cdot 7H_2O$ and NaCl.

6. The method as claimed in claim 1 wherein the fermentation includes fermenting the carbon source inside a batch bioreactor at 7.0 initial culture pH, 30° C. culture temperature and 200 rpm agitation speed for 72 hr.

7. The method as claimed in claim 1 wherein the recovering the biopolymer includes lysing cells using a 5% sodium hypochlorite solution at 37° C. for 90 min and separating the biopolymer by removing impurities.

8. The method as claimed in claim 7 wherein removing impurities include centrifuging and washing cell lysate one or more times followed by purifying the biopolymer.

9. The method as claimed in claim 1 wherein the organic solvent includes toluene, acetone, chloroform, ethylene carbonate, or a combination thereof.

* * * * *